United States Patent
Lee et al.

(10) Patent No.: US 11,167,271 B2
(45) Date of Patent: Nov. 9, 2021

(54) METHOD FOR PRODUCING FERRITE-BASED COATED CATALYST AND METHOD FOR PRODUCING BUTADIENE BY USING SAME

(71) Applicant: LG Chem, LTD., Seoul (KR)

(72) Inventors: Joohyuck Lee, Daejeon (KR); Dong Hyun Ko, Daejeon (KR); Kyong Yong Cha, Daejeon (KR); Myungji Suh, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days.

(21) Appl. No.: 16/964,571

(22) PCT Filed: Feb. 26, 2019

(86) PCT No.: PCT/KR2019/002315
§ 371 (c)(1),
(2) Date: Jul. 23, 2020

(87) PCT Pub. No.: WO2019/177286
PCT Pub. Date: Sep. 19, 2019

(65) Prior Publication Data
US 2021/0039075 A1 Feb. 11, 2021

(30) Foreign Application Priority Data

Mar. 13, 2018 (KR) .................. 10-2018-0029251

(51) Int. Cl.
*B01J 23/00* (2006.01)
*B01J 23/745* (2006.01)
*B01J 37/02* (2006.01)
*C07C 5/48* (2006.01)
*C07C 11/167* (2006.01)

(52) U.S. Cl.
CPC ......... *B01J 23/745* (2013.01); *B01J 37/0215* (2013.01); *C07C 5/48* (2013.01); *C07C 11/167* (2013.01); *C07C 2523/745* (2013.01)

(58) Field of Classification Search
CPC ...... B01J 37/0215; B01J 37/03; B01J 23/745; B01J 23/76; B01J 37/031; C07C 11/167; C07C 5/3332; C07C 2523/745
See application file for complete search history.

(56) References Cited

U.S. PATENT DOCUMENTS

| | | | |
|---|---|---|---|
| 3,951,869 A | 4/1976 | Baker | |
| 4,058,577 A | 11/1977 | Baker | |
| 4,312,787 A | 1/1982 | Dolhyj et al. | |
| 4,806,513 A | 2/1989 | McDaniel et al. | |
| 9,550,174 B2 * | 1/2017 | Kwon | ............ C07C 5/48 |
| 2008/0214863 A1 | 9/2008 | Cremer et al. | |

(Continued)

FOREIGN PATENT DOCUMENTS

| EP | 3222347 A1 | 9/2017 |
|---|---|---|
| EP | 3269448 A2 | 1/2018 |

(Continued)

*Primary Examiner* — Sharon Pregler
(74) *Attorney, Agent, or Firm* — Dentons US LLP

(57) ABSTRACT

The method for preparing a ferrite-based coating catalyst including mixing a support, a ferrite-based catalyst, and water in a coating machine which is a rotating body, in which a weight ratio of the water based on a total weight of the support is 0.15 to 0.3.

4 Claims, 3 Drawing Sheets

(56) References Cited

U.S. PATENT DOCUMENTS

| | | |
|---|---|---|
| 2013/0158325 A1 | 6/2013 | Kwon et al. |
| 2018/0186711 A1 | 7/2018 | Suh et al. |
| 2018/0290126 A1 | 10/2018 | Kim et al. |
| 2018/0333702 A1 | 11/2018 | Suh et al. |
| 2019/0201876 A1 | 7/2019 | Suh et al. |
| 2019/0329226 A1 | 10/2019 | Suh et al. |
| 2020/0122126 A1 | 4/2020 | Suh et al. |

FOREIGN PATENT DOCUMENTS

| | | |
|---|---|---|
| EP | 3441139 A1 | 2/2019 |
| JP | S58-36635 A | 3/1983 |
| JP | 2004-516132 | 6/2004 |
| JP | 2013-536066 | 9/2013 |
| JP | 2015-166088 | 9/2015 |
| KR | 10-1985-0008175 | 12/1985 |
| KR | 10-2012-0009687 | 2/2012 |
| KR | 10-1340620 | 12/2013 |
| KR | 10-2014-0082869 | 7/2014 |
| KR | 10-2017-0068351 | 6/2017 |
| KR | 10-2017-0119051 | 10/2017 |
| KR | 10-2017-0138124 | 12/2017 |
| KR | 10-2018-0115227 | 10/2018 |
| WO | 2018-190641 | 10/2018 |
| WO | 2018-190642 | 10/2018 |
| WO | 2019-107884 | 6/2019 |

\* cited by examiner

[Figure 1]
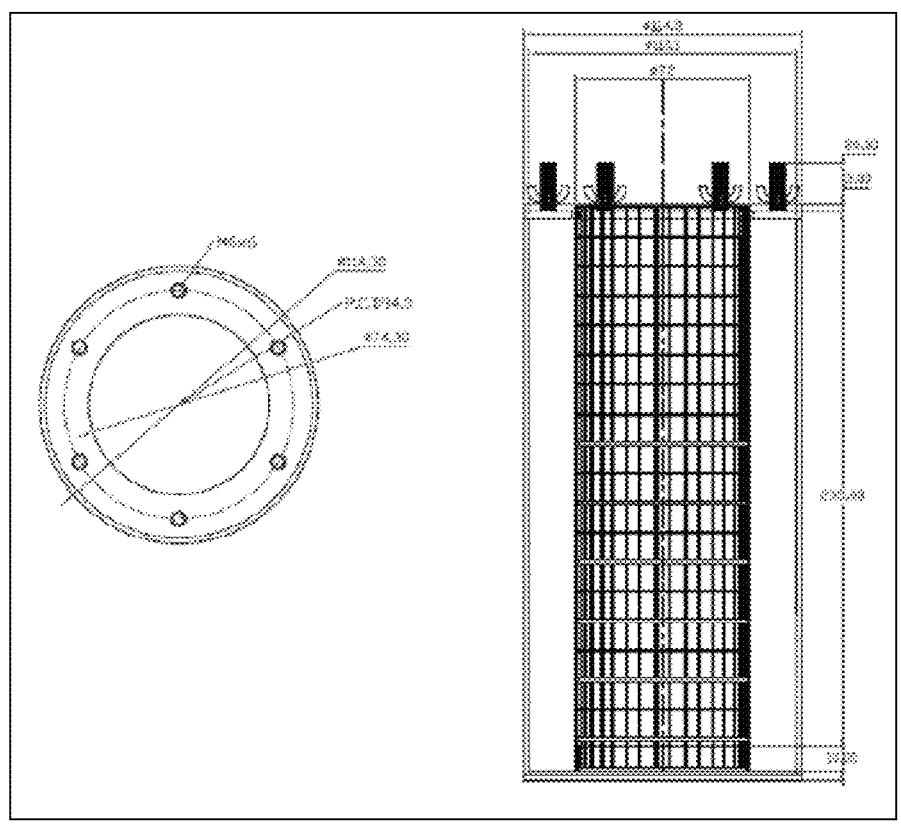

[Figure 2]
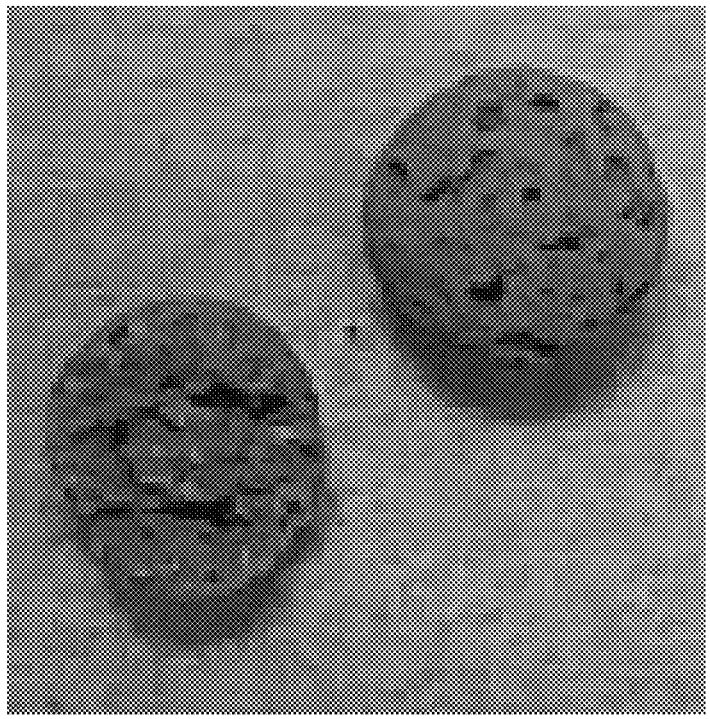
[Figure 3]
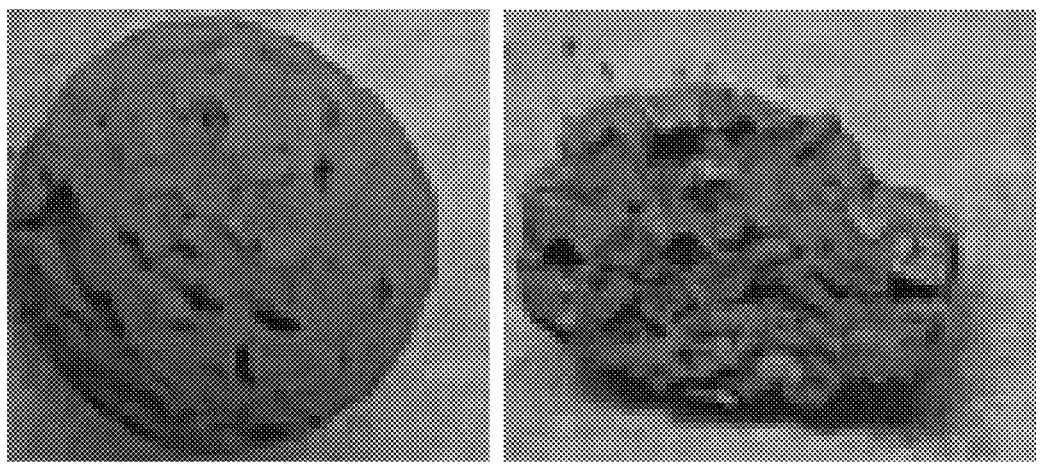

[Figure 4]
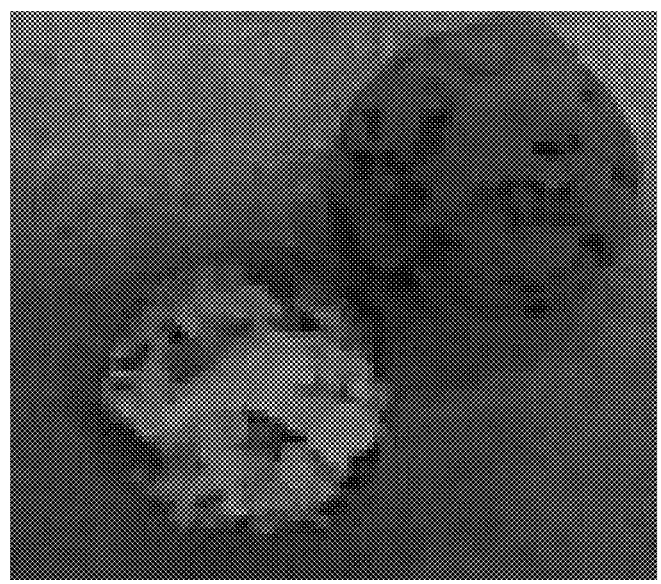

METHOD FOR PRODUCING FERRITE-BASED COATED CATALYST AND METHOD FOR PRODUCING BUTADIENE BY USING SAME

This application is a National Stage Application of International Application No. PCT/KR2019/002315 filed on Feb. 26, 2019, which claims priority to and the benefit of Korean Patent Application No. 10-2018-0029251 filed in the Korean Intellectual Property Office on Mar. 13, 2018, the entire contents of which are incorporated herein by reference.

TECHNICAL FIELD

The present application relates to a method for preparing a ferrite-based coating catalyst and a method for preparing butadiene using the same.

BACKGROUND 1,3-butadiene is an intermediate of petroleum chemical products, and demands for 1,3-butadiene and the value thereof are gradually increasing globally. The 1,3-butadiene has been prepared by using naphtha cracking, the direct dehydrogenation reaction of butene, the oxidative dehydrogenation reaction of butene, and the like.

However, since the naphtha cracking process consumes a lot of energy due to high reaction temperature, and is not a single process only for producing 1,3-butadiene, there is a problem in that other fundamental fractions in addition to 1,3-butadiene are produced in excess. Further, the direct dehydrogenation reaction of n-butene is thermodynamically unfavorable and requires high temperature and low pressure conditions for producing 1,3-butadiene at high yield as an endothermic reaction, and thus is not suitable as a commercialization process for producing 1,3-butadiene.

Meanwhile, the oxidative dehydrogenation reaction of butene is a reaction in which butene and oxygen react with each other in the presence of a metal oxide catalyst to produce 1,3-butadiene and water, and has a very thermodynamically favorable advantage because stable water is produced. Further, since the oxidative dehydrogenation reaction of butene is an exothermic reaction unlike the direct dehydrogenation reaction of butene, 1,3-butadiene can be obtained at high yield even at low reaction temperature as compared to the direct dehydrogenation reaction, and the oxidative dehydrogenation reaction of butene can become an effective single production process capable of satisfying the demands for 1,3-butadiene because an additional heat supply is not required.

The metal oxide catalyst is generally synthesized by a co-precipitation method of preparing the catalyst by simultaneously precipitating a metal solution with a basic solution. Among metal oxide catalysts used in an oxidative dehydrogenation reaction of normal-butene known so far, ferrite-based catalysts are known as being excellent in activity and stability. However, ferrite-based catalysts have a problem in that the activity or durability thereof deteriorates due to excessive heat generation caused by the reaction conditions of high temperature/high pressure, and furthermore, have a problem in that since a side reaction in which COx is produced is promoted, the amount of heat generated is further increased, so that the selectivity of butadiene is decreased in addition to the deterioration in activity or durability of the catalyst.

In order to solve the problems, technologies of controlling heat generation, such as dissipation of generated heat by mixing inert materials such as an aluminum ball, have been reported, but it is known that the effect of reducing heat generation is insignificant, and particularly, in a bulk reaction where the amount of butadiene produced is considerable, it is more difficult to control heat generation of ferrite-based catalysts. In addition, a phenomenon in which the activity rather deteriorates as an additive is introduced is also discovered.

Therefore, there is an urgent need for developing a method for preparing a catalyst capable of improving the physical strength of the catalyst without affecting the selectivity or yield of butadiene under high temperature and high pressure reaction conditions.

Technical Problem

The present application has been made in an effort to provide a method for preparing a ferrite-based catalyst and a method for preparing butadiene using the same.

In particular, an object of the present application is to provide a coating catalyst for an oxidative dehydrogenation reaction capable of more effectively controlling heat generation when the coating catalyst is used for a commercialized reaction in which the amount of butadiene produced is equal to or more than the amount at the laboratory level, and a preparation method thereof.

Further, an object of the present application is to provide a preparation method which improves the physical strength of the catalyst while maintaining the yield or selectivity of butadiene by using the coating catalyst.

The object and other objects of the present application can be all achieved by the detailed description of the present application to be described below.

Technical Solution

An exemplary embodiment of the present application provides a method for preparing a ferrite-based coating catalyst, the method comprising:

mixing a support, a ferrite-based catalyst, and water in a coating machine which is a rotating body, in which a weight ratio of the water based on a total weight of the support is 0.15 to 0.3.

Further, another exemplary embodiment of the present application provides a method for preparing butadiene, the method comprising:

preparing the ferrite-based coating catalyst prepared by the preparation method; and preparing butadiene by using the ferrite-based coating catalyst in an oxidative dehydrogenation reaction of butene.

Advantageous Effects

According to an exemplary embodiment of the present application, during the preparation of a ferrite-based coating catalyst, it is possible to improve the strength of the ferrite-based coating catalyst by introducing water at a specific weight ratio. Accordingly, during the preparation of butadiene using the ferrite-based coating catalyst, it is possible to prevent the loss of the catalyst caused by attrition.

Furthermore, the ferrite-based coating catalyst prepared according to an exemplary embodiment of the present application can improve the catalyst strength while maintaining the catalytic activity.

BRIEF DESCRIPTION OF THE DRAWINGS

FIG. 1 is a view illustrating an attrition test device applied to an Experimental Example of the present application.

FIGS. 2 to 4 are views illustrating the internal states of the coating catalysts of Examples and Comparative Examples of the present application.

DETAILED DESCRIPTION

Hereinafter, the present application will be described in more detail.

In the present specification, the 'yield (%)' is defined as a value obtained by dividing the weight of 1,3-butadiene, which is a product of an oxidative dehydrogenation reaction, by the weight of butene which is a raw material. For example, the yield can be represented by the following equation.

Yield (%)=[(the number of moles of 1,3-butadiene produced)/(the number of moles of butene supplied)]×100

In the present specification, the 'conversion (%)' refers to a rate at which a reactant is converted into a product, and for example, the conversion of butene can be defined by the following equation.

Conversion (%)=[(the number of moles of butene reacting)/(the number of moles of butene supplied)]×100

In the present specification, the 'selectivity (%)' is defined as a value obtained by dividing the change amount of butadiene (BD) by the change amount of butene (BE). For example, the selectivity can be represented by the following equation.

Selectivity (%)=[(the number of moles of 1,3-butadiene or COx produced)/(the number of moles of butene reacting)]×100

Amount of catalyst coated (wt %)=[(mass of ferrite-based catalyst, g)/(mass of support, g+mass of ferrite-based catalyst, g)]×100

Rate of catalyst lost (wt %)=[(mass before attrition experiment, g−mass after attrition experiment, g)/(mass before attrition experiment, g×amount of catalyst coated, wt %)]×100

The present inventors confirmed that when a catalyst was prepared by preparing a metal oxide and coating a support with the metal oxide, the reactivity was excellent and the selectivity of a product was excellent because the surface area of the catalyst per unit volume was large during an oxidative dehydrogenation reaction, thereby completing the present invention based on this finding.

During the preparation of a ferrite-based coating catalyst in the related art, the ferrite-based coating catalyst was prepared by putting a support and a ferrite-based catalyst into a coating machine and coating the outer surface of the support with the catalyst. However, in this method, the catalyst is present only on the outer surface of the support, and the catalyst strength is reduced.

In order to solve the problem, the ferrite-based coating catalyst can be prepared by introducing a support and a catalyst into a rotary evaporator, and then evaporating water under reduced pressure, and in this case, the catalyst strength can be easily improved. However, as the amount of catalyst coated onto the support was increased, the effect of improving the strength was decreased, and further, the method for preparing a ferrite-based coating catalyst in the related art had a problem in that decompression equipment was needed during the mass production of the ferrite-based coating catalyst.

The method for preparing a ferrite-based coating catalyst according to an exemplary embodiment of the present application comprises: mixing a support, a ferrite-based catalyst, and water in a coating machine which is a rotating body, in which a weight ratio of the water based on a total weight of the support is 0.15 to 0.3.

According to an exemplary embodiment of the present application, during the preparation of a ferrite-based coating catalyst, it is possible to improve the strength of the ferrite-based coating catalyst by introducing water at a specific weight ratio. Accordingly, during the preparation of butadiene using the ferrite-based coating catalyst, it is possible to prevent the loss of the catalyst caused by attrition.

In an exemplary embodiment of the present application, the weight ratio of the water based on the total weight of the support can be 0.15 to 0.3, and can be 0.18 to 0.25. When the weight ratio of the water based on the total weight of the support is less than 0.15, only the outer surface of the support is coated with the catalyst, so that the catalyst strength can be reduced, and when the weight ratio of the water based on the total weight of the support is more than 0.3, the support and the catalyst are immersed in water, so that the support cannot be coated with the catalyst.

In an exemplary embodiment of the present application, the mixing of the support, the ferrite-based catalyst, and the water is performed in a coating machine which is a rotating body. The coating machine is not particularly limited, and those known in the art can be used.

In an exemplary embodiment of the present application, the ferrite-based catalyst can be a compound of Formula 1.

$$AFe_2O_4 \qquad \text{Formula 1}$$

In Formula 1, A is Cu, Ra, Ba, Sr, Ca, Cu, Be, Zn, Mg, Mn, Co, or Ni.

In an exemplary embodiment of the present application, it is preferred that the ferrite-based catalyst is a zinc ferrite catalyst.

In an exemplary embodiment of the present application, the content of the ferrite-based catalyst in the ferrite-based coating catalyst can be 10 wt % to 40 wt %, and 12 wt % to 35 wt % based on the total weight of the ferrite-based coating catalyst. When the content of the ferrite-based catalyst is less than 10 wt % or more than 40 wt % based on the total weight of the ferrite-based coating catalyst, the effect of improving the catalytic activity is insignificant, and when the content thereof satisfies the above range, it is possible to prepare a ferrite-based coating catalyst with the improved catalyst strength while maintaining the catalytic activity.

In an exemplary embodiment of the present application, the support can comprise one or more of alumina, silica, cordierite, titania, zirconia, silicon nitride, and silicon carbide. In an exemplary embodiment of the present application, it is preferred that the support is alumina.

The form of the support is not particularly limited, and for example, the support can be alumina in the form of a sphere, and in this case, the diameter thereof can be 2 mm to 7 mm.

In an exemplary embodiment of the present application, the method can further comprise drying the resulting mixture after the mixing of the support, the ferrite-based catalyst, and the water. The method can further comprise firing the mixture after the drying, if necessary. The drying can be performed under the temperature conditions of room temperature, 50° C. to 150° C., 90° C. to 120° C., and the like, but the temperature conditions are not limited thereto.

Further, an exemplary embodiment of the present application provides a method for preparing butadiene, the method comprising: preparing a ferrite-based coating catalyst prepared by the preparation method; and preparing butadiene by using the ferrite-based coating catalyst in an oxidative dehydrogenation reaction of butene.

The oxidative dehydrogenation reaction means a reaction of producing conjugated diene and water by allowing olefin and oxygen to react with each other in the presence of a ferrite-based coating catalyst, and can be a reaction of producing 1,3-butadiene and water by allowing butene and oxygen to react with each other, as a specific example.

A reactor used in the oxidative dehydrogenation reaction is not particularly limited as long as the reactor can be used in the oxidative dehydrogenation reaction, but as an example, the reactor can be a reactor in which the reaction temperature of a catalyst layer installed therein is constantly maintained and the oxidative dehydrogenation reaction is performed while a reactant successively passes through the catalyst layer, and as a specific example, the reactor can be a tubular reactor, a batch-type reactor, a fluidized bed reactor, or a fixed bed reactor, and an example of the fixed bed reactor can be a multi-tubular reactor or a plate-type reactor.

According to an exemplary embodiment of the present application, the preparing of the butadiene can be performed at a reaction temperature of 250° C. to 450° C., 300° C. to 430° C., or 350° C. to 425° C. by using a raw material comprising C4 fractions, steam, oxygen ($O_2$), and nitrogen ($N_2$), and within the above range, the reaction efficiency is excellent without significantly increasing the energy costs, which makes it possible to provide butadiene with high productivity, and maintain the catalytic activity and stability at high levels.

The oxidative dehydrogenation reaction can be performed at a gas hourly space velocity (GHSV) of 50 $h^{-1}$ to 2,000 $h^{-1}$, 50 $h^{-1}$ to 1,500 $h^{-1}$, or 50 $h^{-1}$ to 1,000 $h^{-1}$ based on normal-butene, as an example, and within the range, the reaction efficiency is excellent, which makes it possible to exhibit effects in that conversion, selectivity, yield, and the like are excellent.

The C4 fractions can mean C4 raffinate-1,2,3 remaining by separating useful compounds from a C4 mixture produced by naphtha cracking, and can mean C4 classes which can be obtained through ethylene dimerization.

According to an exemplary embodiment of the present specification, the C4 fractions can be one or a mixture of two or more selected from the group consisting of n-butane, trans-2-butene, cis-2-butene, and 1-butene.

According to an exemplary embodiment of the present specification, the steam or nitrogen ($N_2$) is a diluted gas introduced for the purpose of reducing the explosion danger of the reactant, preventing coking of the catalyst, removing the reaction heat, and the like, in the oxidative dehydrogenation reaction.

According to an exemplary embodiment of the present specification, the oxygen ($O_2$) is an oxidant and reacts with C4 fractions to cause a dehydrogenation reaction.

According to an exemplary embodiment of the present specification, the oxidative dehydrogenation reaction can proceed according to the following Reaction Formula 1 or Reaction Formula 2.

$$C_4H_8 + \tfrac{1}{2}O_2 \rightarrow C_4H_6 + H_2O \qquad \text{Reaction Formula 1}$$

$$C_4H_{10} + O_2 \rightarrow C_4H_6 + 2H_2O \qquad \text{Reaction Formula 2}$$

Hydrogen of butane or butene is removed by the oxidative dehydrogenation reaction, and as a result, butadiene is prepared. Meanwhile, the oxidative dehydrogenation reaction can produce a side reaction product comprising carbon monoxide (CO), carbon dioxide ($CO_2$), or the like, in addition to the main reaction such as Reaction Formula 1 or 2. The oxidative dehydrogenation reaction can comprise a process in which the side reaction product is separated so as not to be continuously accumulated in the process, and is released out of the system.

According to an exemplary embodiment of the present specification, in the method for preparing butadiene, the conversion of butene can be 72% or more, preferably 72.5% or more, and more preferably 79% or more.

According to an exemplary embodiment of the present specification, in the method for preparing butadiene, the selectivity of butadiene can be 85% or more, preferably 85.8% or more, and more preferably 87% or more.

EXEMPLARY EMBODIMENTS

Hereinafter, the present application will be described in detail with reference to Examples for specifically describing the present application. However, the Examples according to the present application can be modified in various forms, and it is not interpreted that the scope of the present application is limited to the Examples described in detail below. The Examples of the present application are provided for more completely explaining the present application to the person with ordinary skill in the art.

EXAMPLES

Example 1

2 L of ammonia water whose pH was adjusted to 8 was prepared, and a metal precursor solution comprising 2 L of distilled water, 288.456 g of zinc chloride ($ZnCl_2$), and 1,132.219 g of iron (III) chloride ($FeCl_3$) was prepared in a separate container. In this case, the molar ratio of the metal components comprised in the metal precursor solution was Fe:Zn=2:1. Ammonia water at a concentration of 9 wt % was together added to the prepared ammonia water in order to maintain the pH to 8 while adding the prepared metal precursor solution to the prepared ammonia water. After the metal precursor solution was completely added while stirring the mixture for 1 hour using a stirrer in order to obtain a sample having the uniform composition, the resulting mixture was aged for 1 hour, and then a solution in which a precipitate was formed was washed by using 4 L of distilled water and simultaneously filtered to separate the precipitate. A co-precipitate was obtained by filtering a co-precipitation solution, which had been thoroughly stirred and aged, under reduced pressure using a vacuum filter, the co-precipitate was washed, and then dried at 90° C. for 24 hours, and then the dried co-precipitate was put into a firing furnace and heat-treated at 650° C. for 6 hours to prepare a zinc ferrite catalyst. A $ZnFe_2O_4$ powder was obtained. The obtained powder was ground and selected by a sieving method so as to have a size of 45 μm or less.

The ferrite-based catalyst, an alumina support in the form of balls having a diameter of 4 mm to 6 mm, and water were introduced together into a coating machine, which is a rotating body, and then mixed to prepare a ferrite-based coating catalyst. In this case, the weight ratio of the introduced water was 0.2 based on the total weight of the support, and the content of the ferrite-based catalyst was 15 wt % based on the total weight of the ferrite-based coating catalyst.

The coated catalyst was dried under a temperature condition of 90° C. to 120° C. for several hours.

Example 2

A ferrite-based coating catalyst was prepared in the same manner as in Example 1, except that the content of the ferrite-based catalyst was adjusted to 25 wt % based on the total weight of the ferrite-based coating catalyst in Example 1.

Example 3

A ferrite-based coating catalyst was prepared in the same manner as in Example 1, except that the content of the ferrite-based catalyst was adjusted to 35 wt % based on the total weight of the ferrite-based coating catalyst in Example 1.

Comparative Example 1

A ferrite-based coating catalyst was prepared in the same manner as in Example 1, except that a rotary evaporator was used without using the coating machine in Example 1. In this case, the vacuum distillation was performed in a state where the support was completely immersed in water by introducing the water such that the weight ratio of the introduced water was 0.6 or more based on the total weight of the support.

Comparative Example 2

A ferrite-based coating catalyst was prepared in the same manner as in Comparative Example 1, except that the content of the ferrite-based catalyst was adjusted to 25 wt % based on the total weight of the ferrite-based coating catalyst in Comparative Example 1.

Comparative Example 3

A ferrite-based coating catalyst was prepared in the same manner as in Example 1, except that a small amount of water was used in Example 1. In this case, the weight ratio of the introduced water was 0.1 or less based on the total weight of the support.

Comparative Example 4

A ferrite-based coating catalyst was prepared in the same manner as in Comparative Example 3, except that the content of the ferrite-based catalyst was adjusted to 25 wt % based on the total weight of the ferrite-based coating catalyst in Comparative Example 3.

Comparative Example 5

A ferrite-based coating catalyst was prepared in the same manner as in Comparative Example 3, except that the content of the ferrite-based catalyst was adjusted to 35 wt % based on the total weight of the ferrite-based coating catalyst in Comparative Example 3.

Comparative Example 6

A ferrite-based coating catalyst was prepared in the same manner as in Example 2, except that in Example 2, water was introduced such that the weight ratio of the introduced water was 0.38 based on the total weight of the support.

EXPERIMENTAL EXAMPLE

As reactants, a mixture of trans-2-butene and cis-2-butene and oxygen were used, and nitrogen and stem were additionally allowed to flow into a reactor together. For the reaction composition, the volume ratios of oxygen, nitrogen, and steam based on butene were 1, 4, and 5, respectively, and the butene was composed such that the component ratios of trans-2-butene and cis-2-butene were 60% and 40% by volume, respectively. The reaction was performed under the conditions of 400° C., GHSV=133 $h^{-1}$, OBR=1, SBR=8, and NBR=1. As the reactor, a metal tubular fixed bed reactor was used. The fixed bed reactor was filled with 200 cc of each of the catalysts prepared in the Examples and the Comparative Examples, steam was infused in the form of water, the water was vaporized into steam at 120° C. by using a vaporizer, the steam was mixed with the butene mixture and oxygen as the reactants, and the resulting mixture was allowed to flow into the reactor. The product after the reaction was analyzed by using gas chromatography (GC), and the conversion of butene, the selectivity of butadiene, the selectivity of COx, and the yield were calculated by using the results measured by gas chromatography.

GHSV: Gas Hourly Space Velocity
OBR: $O_2$/butene molar ratio
SBR: Steam/butene molar ratio
NBR: $N_2$/butene molar ratio The degree of the catalyst lost was evaluated by using an attrition test device in the following FIG. 1, and the results are shown in the following Table 1. More specifically, the rate of catalyst lost was calculated by putting the prepared coating catalyst into the attrition test device, rotating the device at a rate of 90 rpm for 5 minutes, and measuring the masses before and after the experiment.

TABLE 1

| Type of catalyst | Catalyst loss (wt %) |
| --- | --- |
| Example 1 | 3.5 |
| Example 2 | 1.4 |
| Example 3 | 5.8 |
| Comparative Example 1 | 8.0 |
| Comparative Example 2 | 20.4 |
| Comparative Example 3 | 33.6 |
| Comparative Example 4 | 37.2 |
| Comparative Example 5 | 40.8 |
| Comparative Example 6 | 19.3 |

Further, the results of calculating the conversion of butene, the selectivity of butadiene, and the like by using GC equipment are shown in the following Table 2. In addition, the internal state of the coating catalyst according to Example 1 is illustrated in the following FIG. 2, the internal state of the coating catalyst according to Comparative Example 1 is illustrated in the following FIG. 3, and the internal state of the coating catalyst according to Comparative Example 3 is illustrated in the following FIG. 4.

As in the results in the following FIGS. 2 to 4, the support could be coated with the coating catalyst according to Example 1 by introducing a larger amount of water than a dry preparation method, such that the catalyst could permeate the inside of the support. Furthermore, the support was also coated with the coating catalyst according to Comparative Example 1 by vacuum-evaporating water in the rotary evaporator, such that the catalyst permeated the inside of the support. However, it can be confirmed that only outer surface of the support is coated with the coating catalyst according to Comparative Example 3. In particular, it can be confirmed that in Comparative Example 6, water is introduced in excess, and as a result, the catalyst strength is reduced. Accordingly, by adjusting the weight ratio of the water to 0.15 to 0.3 based on the total weight of the support during the preparation of the ferrite-based coating catalyst as in the present application, it is possible to improve the catalyst strength of the ferrite-based coating catalyst while maintaining the catalytic activity thereof.

TABLE 2

| | Type of catalyst | | | |
|---|---|---|---|---|
| | Reaction temperature (° c.) | Conversion (%) of butene (%) | Selectivity of butadiene (%) | Selectivity of CO$x$ (%) |
| Example 1 | 365 | 76.3 | 84.3 | 14.6 |
| Comparative Example 1 | 335 | 79.3 | 83.7 | 14.1 |
| Comparative Example 3 | 335 | 77.0 | 84.1 | 14.7 |

As in the results, in an exemplary embodiment of the present application, it can be confirmed that the attrition property is improved by introducing a suitable amount of water during the preparation of the ferrite-based coating catalyst.

Furthermore, the ferrite-based coating catalyst according to an exemplary embodiment of the present application had a catalytic activity equivalent to those of the catalysts in the related art.

Although the preferred exemplary embodiments of the present invention have been described above, the present invention is not limited thereto, and various modifications can be made and carried out within the scope of the claims and the detailed description of the invention, and also fall within the scope of the invention.

The invention claimed is:

1. A method for preparing a ferrite-based coated catalyst, the method comprising:
    mixing in a coating machine that is a rotating body:
        a support comprising one or more of alumina, silica, cordierite, titania, zirconia, silicon nitride, and silicon carbide,
        a ferrite-based catalyst of Formula 1:

$$AFe_2O_4 \qquad \text{Formula 1}$$

wherein A is Cu, Ra, Ba, Sr, Ca, Be, Zn, Co, or Ni, and water,
    wherein a ratio of the weight of the water to the weight of the support is 0.15 to 0.3.

2. The method of claim 1, wherein a content of the ferrite-based catalyst in the ferrite-based coated catalyst is 10 wt % to 40 wt % based on a total weight of the ferrite-based coating catalyst.

3. The method of claim 1, further comprising: drying the resulting mixture after the mixing of the support, the ferrite-based catalyst, and the water.

4. A method for preparing butadiene, the method comprising:
    preparing a ferrite-based coating catalyst prepared by the preparation method of claim 1; and
    preparing butadiene in a reactor containing the ferrite-based coating catalyst via an oxidative dehydrogenation reaction of butene.

* * * * *